United States Patent [19]

Hoffman

[11] Patent Number: 5,576,203
[45] Date of Patent: Nov. 19, 1996

[54] MODIFIED 7S LEGUME SEED STORAGE PROTEINS

[75] Inventor: Leslie M. Hoffman, Madison, Wis.

[73] Assignee: Mycogen Plant Sciences, Inc., San Diego, Calif.

[21] Appl. No.: 476,743

[22] Filed: Jun. 7, 1995

Related U.S. Application Data

[62] Division of Ser. No. 626,682, Dec. 12, 1990, which is a division of Ser. No. 902,223, Aug. 29, 1986, Pat. No. 5,003,045.

[51] Int. Cl.$^6$ .............................. C12N 15/29; C12N 5/14; C12N 15/82; A01H 5/00
[52] U.S. Cl. .................................... 435/172.3; 435/172.1; 800/205; 800/255; 800/DIG. 70; 530/370; 536/23.6
[58] Field of Search .............................. 435/172.1, 172.3; 800/205, DIG. 70, 255; 536/23.6; 530/370

[56] References Cited

U.S. PATENT DOCUMENTS

| | | | |
|---|---|---|---|
| 4,771,002 | 9/1988 | Gelvin .................................. | 435/172.3 |
| 4,886,878 | 12/1989 | Larkins et al. ....................... | 435/172.3 |

OTHER PUBLICATIONS

Hoffman et al 1988 Pl Molec Biol 11:717–729.
Pedersen et al 1986 (15 May) J Biol Chem 261:6279–6284.
Seugupta–Gopalan 1985 (May) Proc Natl Acad Sci USA 82:3320–3324.
Schuler et al 1982 Nucleic Acids Res 10:8245–8260.
Schuler et al 1982 Nucleic Acids Res 10:8225–8244.
Doyle et al 1986 (May) J Biol Chem 261(20):9228–9238.
Argos et al 1985 (May) The EMBO Journal 4:1111–1117.
Cramer et al 1985 (Jan.) Proc Natl Acad Sci USA 82:334–338.
Cray et al 1982 Nature 295:76–78.
Slighton et al 1985 (Sep.) Nucleic Acids Res 13:6483–6498.
Slighton et al 1983 Proc Natl Acad Sci USA 80:1897–1901.
Larkins et al 1983 In Genetic Eng of Plants, an Agric Perspective, pp. 93–118.
Nielsen 1985 (Jun.) In World Soybean Res Conf III: Proc.; Shibles ed. pp. 281–290.
Goodman et al 1985 (Jun) In World Soybean Res Conf III: Proc.; Shibles ed. pp. 261–271.

*Primary Examiner*—Patricia R. Moody
*Attorney, Agent, or Firm*—Saliwanchik & Saliwanchik

[57] ABSTRACT

The present invention discloses plant cells which contain modified 7S legume seed storage protein. Modification of 7S seed storage proteins which are expressible in plant cells and transformation of such genes into plant cells is also taught. Furthermore, methods and DNA molecules useful for producing plant cells containing modified 7S seed storage proteins are also disclosed. The invention is exemplified by insertion of an oligonucleotide encoding 15 amino acid residues, including 6 methionines, into a *Phaseolus vulgaris* phaseolin gene, thereby tripling its content of sulfur-containing amino acids.

4 Claims, 1 Drawing Sheet

5,576,203

MODIFIED 7S LEGUME SEED STORAGE PROTEINS

This is a division of application Ser. No. 07/626,682 pending, filed Dec. 12, 1990, which is a divisional of U.S. patent application Ser. No. 06/902,223, filed Aug. 29, 1986, now U.S. Pat. No. 5,003,045, which is hereby incorporated by reference.

FIELD OF THE INVENTION

The present invention is in the fields of genetic engineering and plant husbandry, and especially provides a means for producing modified 7S legume seed storage proteins in a plant by transforming a plant to contain a modified 7S legume seed storage protein gene. Also provided are plant-transforming prokaryotic plasmid vectors carrying such modified seed storage genes and plant cells transformed by such a vector.

BACKGROUND OF THE INVENTION

Overview of Agrobacterium

Reviews of Agrobacterium-caused disease, plant transformation, genetic engineering, and gene expression include those by, or found in, Merlo, D. J. (1982) Adv. Plant Pathol. 1:139–178; Ream, L. W. and Gordon, M. P. (1982) Science 218:854–859; Bevan, M. W. and Chilton, M-D. (1982) Ann. Rev. Genet. 16:357–384; Kahl, G. and Schell, J. (1982) *Molecular Biology of Plant Tumors*; Barton, K. A. and Chilton, M-D. (1983) Methods Enzymol. 101:527–539; Weissbach, A. and Weissbach, H. (eds.) (1986) Methods Enzymol. 118 (see especially, Rogers, S. G. et al., pp. 627–640); Depicker, A. et al. (1983) in *Genetic Engineering of Plants: an Agricultural Perspective*, Kosuge, T. et al. (eds.), pp. 143–176; Caplan, A. et al. (1983) Science 222:815–821; Hall, T. C. et al., European Patent Application 126,546; and Binns, A. N. (1984) Oxford Surveys Plant Mol. Biol. 1:130–160; Hall, T. C. Oxford Surveys Plant Mol. Biol. 2:329–338; Hooykaas, P. J. J. and Schilperoort, R. A. (1985) Trends Biochem. Sci. 10:307–309; Thomas, T. L. and Hall, T. C. (1985) Bioassays 3:149–153; Puhler, A. (ed.) (1983) *Molecular Genetics of the Bacteria-Plant Interaction*; and Schilperoort, R. A. (1984) in *Efficiency in Plant Breeding* (Proc. 10th Congr. Eur. Assoc. Res. Plant Breeding), Lange, W. et al. (eds.), pp. 251–285.

Transformation of Plants by Agrobacterium

Plant cells can be transformed by Agrobacterium by several methods well-known in the art. For a review of recent work, see Syono, K. (1984) Oxford Surveys Plant Mol. Cell Biol. 1:217–219. Inoculation of leaf disks is particularly advantageous (Horsch, R. B. et al. (1985) Science 227:1229–1231)

The host range of crown gall pathogenesis may be influenced by T-DNA-encoded functions such as onc genes (Hoekema, A. et al. (1984) J. Bacteriol. 158:383–385; Hoekema, A. et al. (1984) EMBO J. 3:3043–3047; Buchholz, W. C. and Thomasshow, M. F. (1984) 160:327–332; Yanofsky, M. (1985) Mol. Gen. Genet. 201:237–246). Vir genes also affect host range (Yanofsky, supra).

Genes on the Transformation-Inducing Plasmids

The complete sequence of the T-DNA of an octopine-type plasmid found in ATCC 15955, pTi15955, has been reported (Barker, R. F. et al. (1983) Plant Mol. Biol. 2:335–350) as has the $T_L$ region of pTiAch5 (Gielen, J. et al. (1984) EMBO J. 3:835–846). Published T-DNA genes do not contain introns. Sequences resemblingcanonical eukaryotic promoter elements and polyadenylation sites can be recognized.

The ocs gene encodes octopine synthase (lysopine dehydrogenase). Koncz, C. et al. (1983) EMBO J. 2:1597–1603 provides a functional analysis of ocs. Dhaese, P. et al. (1983) EMBO J. 2:419–426, reported the utilization of various polyadenylation sites by "transcript 7" (ORF3 of Barker, R. et al., supra) and ocs.

The nos gene encodes nopaline synthase (sequenced by Depicker, A. et al. (1982) J. Mol. Appl. Genet. 1:561–573). Shaw, C. H. et al. (1984) Nucl. Acids Res. 12:7831–7846; and An, G. et al. (1986) Mol. Gen. Genet. 203:245–250, provide functional analyses of nos.

Ti and Ri plasmid genes outside of the T-DNA region include the vir genes which, when mutated, result in an avirulent Ti plasmid. The vir genes function in trans, being capable of causing the transformation of plant cells with T-DNA of a different plasmid type and physically located on another plasmid. Such arrangements are known as binary systems and the T-DNA-bearing plasmids are generally known as micro-Ti plasmids. Many binary systems are known to the art. T-DNA need not be on a plasmid to transform a plant cell; chromosomally-located T-DNA is functional (Hoekema, A. et al. (1984) EMBO J. 3:2485–2490). Ti plasmid-determined characteristics have been reviewed by Merlo, supra (see especially Table II), and Ream and Gordon, supra.

Seed Storage Protein Expression

A gene encoding bean phaseolin has been transferred into and expressed in sunflower tumors. Transcription started and stopped at the correct positions, and introns were posttranscriptionally processed properly (Murai, N. et al. (1983) Science 222:476–482). The phaseolin gene was expressed at a high-level in developing tobacco seeds (Sengupta-Gopalan, C. et al. (1985) Proc. Natl. Acad. Sci. U.S.A. 82:3320–3324). Similar results have been observed with soybean β-conglycinin which is about 60% homologous with the phaseolin gene (Beachy, R. N. et al. (1985) EMBO J. 4:3047–3053). Some genes for the endosperm protein zein, from the monocot Zea mays, are transcribed in dicot cells, though translational products of these transcripts have not been detected (Matzke, M. A. et al. (1984) EMBO J. 3:1525–1531; Goldsbrough et al. (1986) Mol. Gen. Genet. 202:374–381). Murai, N. et al. (1983) Science 222.:476–482, reported fusion of the ocs promoter and its structural gene's 5'-end to a phaseolin structural gene, and expression thereof.

Legume Storage Proteins

A seed storage protein is a protein present in a seed having as its primary function the storage of amino acids for use by a seedling derived after germination of that seed to make other proteins. Legume storage proteins are reviewed by Derbyshire, E. et al. (1976) Phytochem. 15:3–24, and Millerd, A. (1975) Ann. Rev. Plant Physiol. 26:53–72. The 7S storage proteins are classified as such because of their sedimentation coefficient (about 7 svedbergs). Doyle, J. J. et al. (1986) J. Biol. Chem. 261:9228–9238, compare sequences of 7S storage proteins from Phaseolus vulgaris (phaseolin), Glycine max (β-conglycinin), and Pisum sativum (vicilin and convicilin). They found that β-type phaseolin and the α' subunit of β-conglyconin have considerable hemology at both the nucleotide and amino acid sequence levels (Doyle et al. (1986) J. Biol. Chem. 261:9228–9238). Doyle et al. compared the degree of apparent nucleotide divergence for 18 regions and found that the overall corrected divergence between these genes is about 41%. Similarly, comparison of protein sequences (Doyle et al., FIG. 2) shows that about 40% or more of those residues are either identical or have conservative substitutions (196 conserved or identical residues out of 509 residues compared).

SUMMARY OF THE INVENTION

It is well-known that most herbivores cannot synthesize all twenty of the amine acids used to make proteins. These amino acids, which must be supplied in the herbivore's diet, are referred to as "essential amine acids." For many species of mammals, the basic amine acids, e.g., lysine, and the sulfur-containing amino acids, i.e., methionine and cysteine, are essential. As cereal seed storage proteins are low in basic amino acids and legume storage proteins are low in sulfur-containing amino acids, mammalian diets often contain a mixture of legumes and grains so that the total amino acid complement consumed is balanced. The ability to express a 7S legume seed storage protein having relatively high levels of methionine in a plant can allow one to create a more nutritious plant having a better mix of amino acids. Therefore, it is an object of the present invention to increase the sulfur-containing amino acid content of a legume storage protein.

Methods are provided for expression of these modified genes in plant cells. Furthermore, DNA molecules useful for this are provided. As exemplified herein, a 7S seed storage protein gene from *Phaseolus vulgaris*, phaseolin, has been modified to contain an insertion of methionine-encoding sequences of a Zea mays seed storage protein zein. This modified gene has been expressed in seeds of *Nicotiana tabacum*. Phaseolin is a globulin (i.e., it is soluble in saline solutions), while zein is a prolamine (i.e., it is soluble in ethanolic solutions).

In particular, one can modify a 7S legume seed storage protein. A modification of the *Phaseolus vulgaris* 7S storage protein phaseolin is exemplified herein, but other 7S storage proteins, Such as the Glycine max protein β-conglycinin, could similarly be modified. The exemplified modificatioh increases the particular phaseolin gene's content of sulfur-containing amino acids, in this case methionine, about three-fold. The modification can be one or more insertions or substitutions. DNA molecules having structural genes encoding such modified 7S legume seed storage protein can also be made. To express such a protein in a plant, one must have the structural gene combined with a promoter and a polyadenylation site; the promoter, the structural gene, and the polyadenylation site being in such position and orientation with respect to each other that the structural gene is expressible in a plant cell under control of the promoter and the polyadenylation site. The promoter and the polyadenylation site are most conveniently derived from the same gene as the structural gene or from another 7S legume storage protein gene. The phaseolin and β-conglycinin genes provide very useful promoters. A plant-expressible modified 7S seed storage protein gene can be transformed into a plant after it has been inserted into a T-DNA, which includes a T-DNA border repeat and a selectable or screenable marker (e.g., a neomycin phosphotransferase gene or an ocs gene). Also disclosed herein is a method for expressing a modified 7S legume seed storage protein in a plant cell by modifying a DNA sequence of a structural gene encoding a 7S legume seed storage protein, transforming a plant cell with the modified structural gene, the modified gene being expressible in a plant cell, and regenerating a plant descended from the transformed plant cell.

It is believed that before this invention there were no published reports of expression of an artificially modified 7S legume seed storage protein structural gene. Before the work presented herein was done, it was not known if, when expressed in a plant cell, a modified 7S legume seed storage globulin would be stable, if it would be glycosylated, if it would undergo proper posttranslational processing, if it would be located in the proper cellular compartment, and if its polypeptide backbone would properly fold.

DETAILED DESCRIPTION OF THE INVENTION

Figure 1:
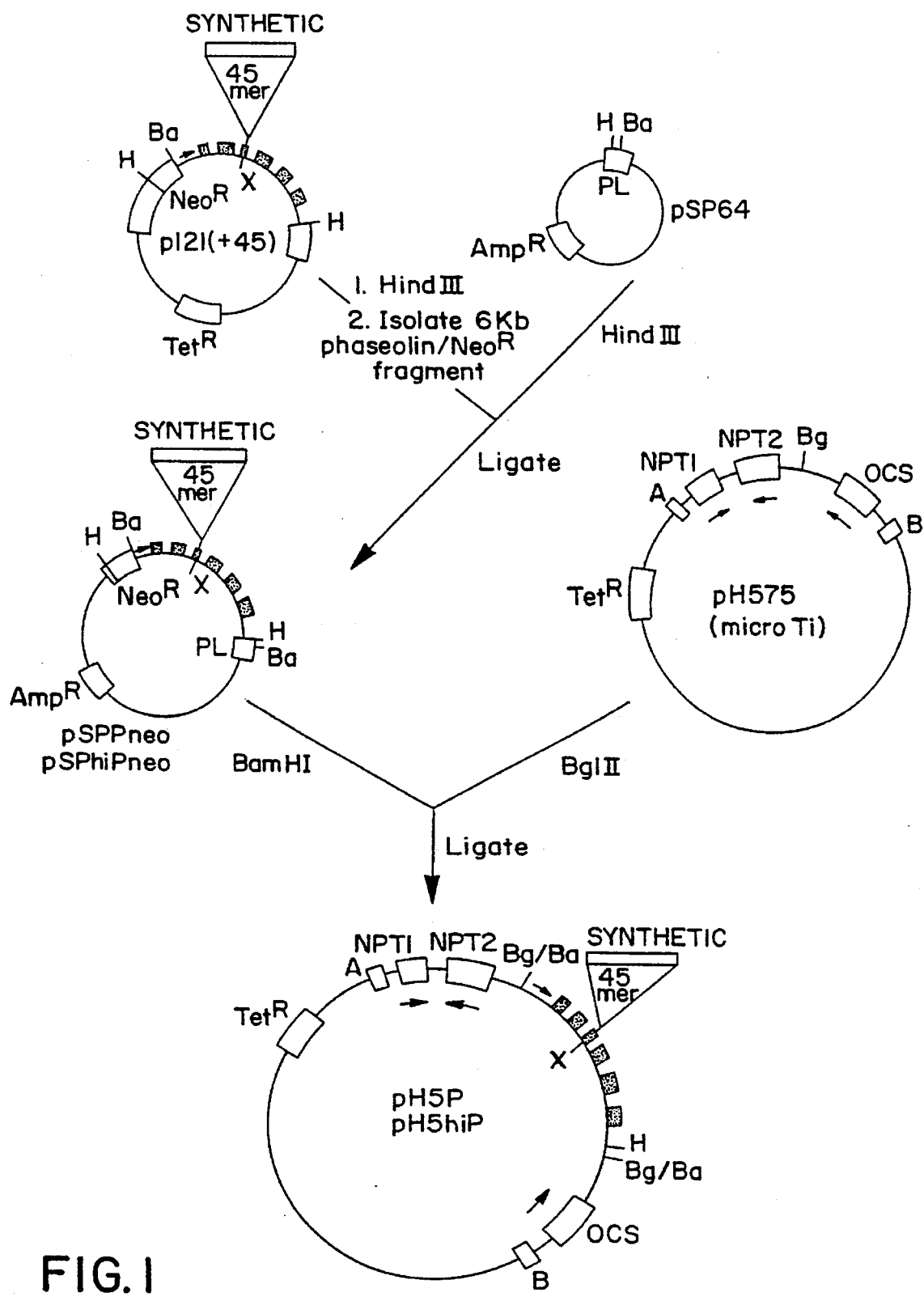
FIG. 1 diagrams, schematically and not necessarily to scale, construction of a micro-Ti plasmid carrying a plant-expressible phaseolin gene which has been modified to have an increased methionine content. Restriction sites have been abbreviated as follows: Ba, BamHI; Bg, BglII; H, HindIII; and X, XbaI. Other abbreviations include $Amp^R$ and $Tet^R$, respectively, for bacterial resistance genes for ampicillin and tetracycline; NPT1 for a bacteria-expressible neomycin phosphotransferase I gene; NPT2 for a plant-expressible neomycin phosphotransferase II gene; PL for a polylinker (a short stretch of DNA having numerous restriction sites); $Neo^R$ for a bacteria-expressible neomycin phosphotransferase II gene; OCS for a plant-expressible octopine synthase gene (ocs); and A and B for the octopine-type $T_L$-DNA A and B border repeats. Phaseolin exons are indicated by the solid-filled boxes. Open boxes indicate the $Tet^R$, $Amp^R$, PL (polylinker), borders A and B, NPT1, NPT2, $Neo^R$ and ocs Additionally for p121(+45) pSPPneo, and pSPhiPneo, open boxes can indicate the location of octopine-type $T_L$-DNA sequences that are not part of an indicated gene or border. Arrows inside a circle indicate the direction of transcription of the indicated gene while the arrow out of the circle next to the filled boxes indicates the location of the phaseolin promoter and its direction of transcription.

The following definitions are provided in order to remove ambiguities to the intent or scope of their usage in the specification and claims.

7S Lequme Seed Storage Protein: Refers to any protein having at least 20% homology to either the nucleic acid or protein sequence of either phaseolin or β-conglycinin.

Modified Protein: Refers to having a different amino acid sequence than a naturally-occurring protein.

Promoter: Refers to sequences at the 5'-end of a structural gene involved in initiation of transcription. A plant-expressible promoter is any promoter capable of driving transcription in at least one type of plant cell in at least one developmental stage. Eukaryotic promoter sequences are commonly recognized by the presence of DNA sequences homologous to the canonical form 5' ... TATAA ... 3' about 10–30 base pairs (bp) 5'-to the location of the 5'-end of the mRNA (cap-site). About 30 bp 5'-to the TATAA, another promoter sequence is often found which is recognized by the presence of DNA sequences homologous to the canonical form 5' . . . CCAAT . . . 3'.

Transcript Terminator: Refers herein to any nucleic acid sequence capable of determining the position of the 3'-end of a transcript. The transcript terminator DNA segment may itself be a composite of segments derived from a plurality of sources, naturally-occurring or synthetic, prokaryotic, or eukaryotic, and may be from a genomic DNA or an mRNA-derived cDNA (mRNA: messenger RNA). Transcript termination sites include polyadenylation sites and. sites determining the 3'-end of ribosomal RNAs (rRNAs), transfer RNAs (tRNAs), and nonpolyadenylated mRNAs (e.g., histone mRNA: Krieg, P. A. and Melton, D. A. (1984) Nature 308:203–206).

A polyadenylation site is a nucleic acid sequence correlated with polyadenylation of mRNA in eukaryotes, i.e., after transcriptional termination polyadenylic acid "tails" are added to the 3'-end of mRNA precursors. Polyadenylation sites are commonly recognized by the presence of homology to the canonical form 5' AATAAA 3', although variations of distance 5' to the 3' -end of the transcript, partial "read-through," and multiple tandem canonical sequences are not uncommon. DNA sequences between 20 and 35 bp downstream from the transcript's 3'-end seem to be necessary (McDevitt, M. A. et al. 1984) Cell 37:993–999). It should be recognized that a canonical "polyadenylation site" may actually determine the location of the 3'-end of the mRNA and not polyadenylation per se (Proudfoot, N. (1984) Nature 307:412–413; Birnstiel, M. L. et al. (1985) Cell 41:349–359).

Transcription Controlling Sequences: Refers to a promoter/transcript terminator site combination flanking a structural gene. The promoter and terminator DNA sequences flanking a particular foreign structural gene need not be derived from the same gene (e.g., pairing two different T-DNA transcripts) or the same taxonomic source (e.g., pairing sequences from T-DNA with sequences from non-T-DNA sources such as plants, animals, fungi, yeasts, eukaryotic viruses, bacteria, and synthetic sequences).

Translational Initiation Site: Refers-herein to the 5'AUG3' translational start codon at the 5'-end of a structural gene, the nucleotide following the AUG, and the 3 nucleotides preceding the AUG (see Kozak, M. (1983) Microbiol. Rev. 47:1–45; and Kozak, M. (1984) Nucl. Acids Res. 12:857–872).

5'-Untranslated Sequence: Refers herein to the part of an mRNA between its 5'-end, or "cap site," and the translational start codon.

3'-Untranslated Sequence: Refers hergin to the part-of an mRNA between its translational stop codon and either its polyadenylic acid segment or the 3'-end of a nonpolyadenylated mRNA.

Plant-Expressible Selectable or Screenable Marker: Refers herein to a genetic marker functional in a plant cell. A selectable marker (e.g., a kanamycin resistance gene) allows cells containing and expressing that marker to grow under conditions unfavorable to growth of cells not expressing that marker. A screenable marker (e.g., a β-galactosidase gene) facilitates identification of cells which express that marker.

Plant-Expressible: Refers to the ability of a gene to be expressed in a plant cell. A gene is plants-expressible if a plant is capable of expressing it in at least one tissue or cell type in at least one developmental stage.

T-DNA: Refers in the art to the DNA sequence between and including two T-DNA border repeats capable of being transferred to a plant cell from a vir gene-containing Agrobacterium cell.

Transforming: Refers to the act of causing a cell to contain a nucleic acid molecule or sequence not originally part of that cell. Often, but not always, a transformation involves insertion of the transformed DNA into the cell's DNA.

Plant Tissue: Includes differentiated and undifferentiated tissues of plants including, but not limited to roots, shoots, pollen, seeds, tumor tissue, such as crown galls, and various forms of aggregations of plant cells in culture, such as embryos and calluses. The plant tissue may be in planta or in organ, tissue, or cell culture.

Plant Cell: As used herein includes plant cells in planta and plant cells and protoplasts in culture.

The following terms are well-known in the art and are not specifically or specially defined herein: insertion, substitution, T-DNA border repeat, transcription under control of a promoter, and structural gene.

Production of a genetically-modified plant cell expressing a modified 7S legume seed storage protein gene combines the specific teachings of the present disclosure with a variety of techniques and expedients known in the art. In most instances, alternative expedients exist for each stage of the overall process. The choice of expedients depends on variables such as the choice of the particular 7S seed storage protein gene, the particular modification, the exact location(s) of the modification(s), the dicot species to be modified, the basic vector system for the introduction and stable maintenance of the promoter/structural gene combination, and the like, all of which present alternative process steps which those of ordinary skill are able to select and use to achieve a desired result. As novel means are developed for the stable insertion and transcription of foreign DNA in plant cells, those of ordinary skill in the art will be able to select among those alternate process steps to achieve a desired result. The fundamental aspects of the invention are the nature of the 7S seed storage protein and the nature of the modification thereof and the use of a gene encoding this storage protein to synthesize this modified protein in cells of plants transformed therewith. Other aspects include the means of insertion and expression of this modified gene in a plant genome. The remaining steps of the preferred embodiment for obtaining genetically-modified plants include inserting the combination into T-DNA, transferring the modified T-DNA to a plant cell wherein the modified T-DNA becomes stably integrated as part of the plant cell genome, techniques for in vitro culture and eventual regeneration into whole plants, which may include steps for selecting and detecting transformed plant cells and steps of transferring the introduced gene combination from the originally transformed strain into commercially-acceptable cultivars, and monitoring expression in transformed plants.

A principal feature of the present invention in its preferred embodiment is the construction of a T-DNA derivative having an inserted modified gene under control of plant-expressible transcription-controlling sequences, i.e., between a promoter and a transcript terminator, as these terms have been defined, supra. The structural gene must be inserted in correct position and orientation with respect to the promoter. Position relates to which side of the promoter the structural gene is inserted. It is known that the majority of promoters control initiation of transcription and translation in one direction only along the DNA. The region of DNA lying under promoter control is said to lie "downstream" or alternatively "behind" or "3' to" the promoter. Therefore, to be controlled by the promoter, the correct position of a structural gene insertion must be "downstream" from the promoter. Orientation refers to the directionality of the structural gene. That portion of a structural gene which encodes the amino terminus of a protein is termed the 5'-end of the structural gene, while that end which encodes amino acids near the carboxyl end of the protein is termed the 3'-end of the structural gene. Correct orientation of the structural gene is with the 5'-end thereof proximal to the promoter. Similarly to the promoter region, the transcript terminator must be located in correct position and orientation relative to the structural gene being proximal to the 3'-end of the structural gene. Differences in rates of gene expression or developmental control may be observed depending on the particular components, e.g., promoters, transcript terminators, flanking DNA sequences, or site of insertion into the transformed plant's genome. Storage protein accumulation may also be affected by storage protein mRNA stability, which can be greatly influenced by mRNA secondary structure, especially stem-loop structures. Different properties, including, but not limited to, such properties as stability, intracellular localization, posttranscriptional processing, and other functional properties of the expressed structural gene itself may be observed when promoter/ structural gene/transcript terminator components are varied. All of these variations present numerous opportunities to manipulate and control the functional properties of the 7S seed storage protein, depending upon the desired physiological properties within the plant cell, plant tissue, and whole plant.

The fundamental principle of the present invention is that modified 7S legume seed storage globulins are capable of being made in plant cells that contain a plant-expressible modified 7S legume seed storage protein gene combination. The requirements for which DNA sequence segments are to be included in such a gene are best couched in functional terms. Transcript terminators, in particular polyadenylation sites, and promoters are understood in the art to be functional termS. However, the art understands a promoter to be that DNA segment capable of initiating transcription. Numerous promoters have been defined by methods such as deletion analysis. A promoter is the smallest continuous DNA segment that is necessary and sufficient to cause RNA polymerase to transcribe a flanking DNA segment. A promoter-bearing DNA segment may contain additional DNA sequences that are not necessary for transcription. Similarly, a polyadenylation site (or other transcript terminator) is functionally defined as the smallest continuous DNA segment that is necessary and sufficient to cause a transcript to become polyadenylated (or otherwise terminated). The functional requirements for a structural gene are also well understood. A structural gene must start with a translational initiation (start, AUG) site, end with a translational termination (stop) codon (UAA, UAG, or UGA) and have an integral number of triplet codons in between, without an intervening stop codon.

The transcript of the modified 7S legume seed storage globulin gene may include heterologous sequences in addition to sequences encoding the modification. Inclusion of various heterologous sequences may affect mRNA stability, cellular localization of the mRNA, posttranscriptional processing, and the like. It is known to the art that RNA stability is affected by terminal structures such as 5'-capping and 3'-polyadenylation and by the extent of internal structure, i.e., intramolecular basepairing. Translational efficiency can similarly be affected by structures in the 5'-untranslated region, and by the exact sequence of the translational initiation site. An intron may be included in an mRNA, provided that, if the splice sites are derived from two different genes, the intron splice sites be compatible.

Combining of DNA segments, including coding, promoter, and transcript terminator sequences, to form a promoter/structural gene/terminator combination is accomplished by means known and understood by those of ordinary skill in the art of recombinant DNA technology. Choice of promoter depends on the developmental regulation desired. Use of developmentally-regulated promoters for gene expression in plants is well-known in the art. T-DNA or cauliflower mosaic virus promoters are advantageous as they are constitutive. The promoter of the gene for the small subunit of ribulose 1,5-bisphosphate carboxylase maybe useful for expression in the green tissues of a plant transformed to contain a promoter/seed storage gene combination. The promoter of seed storage protein gene (e.g., phaseolin) can be used to express a monocot seed storage protein structural gene in plant seeds including seed of nonlegumes (e.g., *Nicotiana tabacum*). In the preferred embodiments, the transcript terminator is a polyadenylation site. The plant gene source of the polyadenylation site is not crucial provided that the polyadenylation site, the promoter and the structural gene are compatible for transcription and posttranscriptional processing.

As will be apparent to those of ordinary skill in the art, the plant-expressible modified gene can be placed between any restriction sites convenient for removing the gene from the plasmid on which it is carried, and convenient for insertion into the plant transformation vector of choice. For example, location of the gene insertion site within T-DNA is not critical as long as the transfer function of sequences immediately surrounding the T-DNA borders are not disrupted, since in prior art studies these regions appear to be essential for insertion of the modified T-DNA into the plant genome. The gene/T-DNA combination is inserted into the plant transformation vector by standard techniques well-known to those skilled in the art. The orientation of the modified gene with respect to the direction of transcription and translation of endogenous vector genes is not usually critical; generally, either of the two possible orientations is functional.

As is well-known in the art, T-DNA of micro-Ti plasmids can be transferred from an Agrobacterium strain to a plant cell provided the Agrobacterium strain contains certain trans-acting genes whose function is to promote the transfer of T-DNA to a plant cell. Micro-Ti plasmids are advantageous in that they are small and relatively easy to manipulate directly, eliminating the need to transfer the gene to T-DNA from a shuttle vector by homologous recombination. After the modified gene has been inserted, the micro-Ti plasmid can easily be introduced directly into an Agrobacterium cell containing trans-acting vir genes, the vir genes usually being on a "helper plasmid," that promotes T-DNA transfer. Introduction into an Agrobacterium strain is conveniently accomplished either by transformation of the Agrobacterium strain or by conjugal transfer from a donor bacterial cell, the techniques for which are well-known to those of ordinary skill. For purposes of introduction of novel DNA sequences into a plant genome, Ti plasmids, Ri plasmids, micro-Ti plasmids, and T-DNA integrated into chromosomes should be considered functionally equivalent.

T-DNA having a modified 7S seed storage protein gene can be transferred to plant cells by any technique known in the art. For example, this transfer is most conveniently accomplished by cocultivation of the Agrobacterium strain with plant cells or with plant tissues. Using these methods, a certain proportion of the plant cells are transformed, that is to say have T-DNA transferred therein and inserted in the plant cell genome. In either case, the transformed cells must be selected or screened to distinguish them from untransformed cells. Selection is most readily accomplished by providing a selectable marker or screenable marker incorporated into the T-DNA in addition to the gene combination. Examples of artificial markers are well-known in the art. In addition, the T-DNA provides endogenous markers such as gene(s) controlling abnormal morphology of Ri-induced tumor roots and gene(s) that control resistance to toxic compounds such as amino acid analogs, such resistance-being provided by an opine synthesizing enzyme (e.g., ocs). Screening methods well-known to those skilled in the art include, but are not limited to, assays for opine production, specific hybridization to characteristic nucleic acid sequences (e.g., storage protein mRNA or T-DNA) or immunological assays for specific proteins (e.g., phaseolin or neomycin phosphotransferase II).

Although the preferred embodiments involve use of micro-Ti plasmids, other T-DNA-based vector systems known to the art may readily be substituted. Furthermore, though the preferred embodiment of this invention incorporates a T-DNA-based Agrobacterium-mediated system for incorporation of the modified 7S seed storage protein gene into the genome of the plant which is to be transformed, other means for transferring and incorporating the modified gene into a plant genome are also included within the scope of this invention. Other means for the stable incorporation of the modified gene into a plant genome additionally include, but are not limited to, use of vectors based upon viral genomes, minichromosomes, transposons, and homologous or nonhomologous recombination into plant chromosomes. Alternate forms of delivery of these vectors into a plant cell additionally include, but are not limited to, fusion with vector-containing liposomes or bacterial spheroplasts, microinjection, encapsidation in viral, coat protein followed by an infection-like process, and direct uptake of DNA, possibly after induction of plasmalemma permeability by an electric pulse, a laser, or a chemical agent. Means for transient incorporation and/or expression are also included within the scope of this invention. SyStems based on Agrobacterium cells and T-DNAs can be used to transform angiosperms, including dicots and monocots, by transfer of DNA from a bacterium to a plant cell; systems based on alternate vectors or means for vector delivery may be used to transform gymnosperms and angiosperms.

Regeneration of transformed cells and tissues is accomplished by resort to known techniques. An object of the regeneration step is to obtain a whole plant that grows and reproduces normally but which retains integrated T-DNA. The techniques of regeneration vary somewhat according to principles known in the art, and may depend upon the plant transformation vector and the species of the transformed plant. Regeneration of transformed tobacco plants, petunia plants, and plants of related species is well-known to the art. As means for regeneration of other plant species are developed, the art will understand, without undue experimentation, how to adapt these newly-discovered means for regeneration of plants from transformed plant cells and transformed plant tissues.

The genotype of the plant tissue transformed is often chosen for the ease with which its cells can be grown and regenerated in in vitro culture and for susceptibility to the selective agent to be used. Should a cultivar of agronomic interest be unsuitable for these manipulations, a more amenable variety is first transformed. After regeneration, the newly introduced gene may be readily transferred to the desired agronomic cultivar by techniques well-known to those skilled in the arts of plant breeding and plant genetics. Sexual crosses of transformed plants with the agronomic cultivars yield initial hybrids. These hybrids can then be back-crossed with plants of the desired genetic background. Progeny are continuously screened and/or selected for the continued presence of the introduced gene, T-DNA, or for a new phenotype resulting from expression of the gene combination or other genes carried by the inserted DNA. In this manner, after a number of rounds of back-crossing and selection, plants can be produced having a genotype essentially identical to the agronomically-desired parents with the addition of inserted DNA sequences.

EXAMPLES

The following Examples are presented for the purpose of illustrating specific embodiments within the scope of the present invention without limiting the scope, the scope being defined by the claims. Numerous variations will be readily apparent to those of ordinary skill in the art.

The Examples utilize many techniques well-known and accessible to those skilled in the arts of molecular biology and manipulation of T-DNA and Agrobacterium; such methods are fully described in one or more of the cited references if not described in detail herein. All references cited in ,this Specification are hereby incorporated by reference. Enzymes are obtained from commercial sources and are used according to the vendors' recommendations and other variations known to the art. Reagents, buffers, and,culture conditions are also known to those in the art. Reference works containing such standard techniques include the following: Wu, R. (ed.) (1979) Methods Enzymol. 68; Wu, R. et al. (eds.) (1983) Methods Enzymol. 100 and 101; Grossman, L. and Moldave, D. (eds.) (1980) Methods Enzymol. 65; Weissbach, A. and Weissbach, H. (eds.) (1986) Methods Enzymol. 118 (see especially, Rogers, S. G. et al., pp. 627–640); Miller, J. H. (1972) *Experiments in Molecular Genetics*; Davis, R. et al. (1980) *Advanced Bacterial Genetics*; Schleif, R. F. and Wensink, P. C. (1982) *Practical Methods in Molecular Biology*; Walker, J. M. and Gaastra, W. (eds.) (1983) *Techniques in Molecular Biology*; and Maniatis, T. et al. (1982) *Molecular Cloning*. Additionally, Lathe, R. F. et al. (1983) Genet. Engin. 4:1–56, make useful comments on DNA manipulations.

Textual use of the name of a restriction endonuclease in isolation, e.g., "BclI," refers to use of that enzyme in an enzymatic digestion, except in a diagram where it can refer to the site of a sequence susceptible to action of that enzyme, e.g., a restriction site. In the text, restriction sites are indicated by the additional use of the word "site," e.g., "BclI site." The additional use of the word "fragment," e.g., "BclI fragment," indicates a linear double-stranded DNA molecule having ends generated by action of the named enzyme (e.g., a restriction fragment). A phrase such as "BclI/SmaI fragment" indicates that the restriction fragment was generated by the action of two different enzymes, here BclI and SmaI, the two ends resulting from the action of different enzymes.

Plasmids, and only plasmid, are prefaced with a "p" e.g., pTi15955 of pH400, and strain designations parenthetically indicate a plasmid harbored within, e.g., A. tumefaciens (pTi15955) or E. coli H802 (pH400). The following strains have been deposited:

| | |
|---|---|
| *A. tumefaciens* (pTi15955) | ATCC 15955 |
| *E. coli* HB101 (p3.8) | NRRL B-15392 |

(ATCC: American Type Culture Collection, 12301 Parklawn Drive, Rockville, Md. U.S.A.; NRRL: ARS Patent Collection, Northern Regional Research Center, 1815 N. University Street, Peoria, Ill. 61614 U.S.A.) Other plasmids and strains are widely available and accessible to those in the art.

Example 1

Construction of a micro-Ti plasmid, pH575 p102, a pBR322 clone of the pTi15955 T-DNA fragment between HindIII sites at positions 602 and 3,390 (as defined by Barker R. F. et al. (1983) Plant Mol. Biol. 2:335–350) carries the left border of $T_L$ and promoter sequences associated with ORF1. p233 is a pBR322 clone of the pTi15955 T-DNA BamHI/EcoRI fragment spanning positions 9,062 and 16,202. The T-DNA of p233 includes a SmaI/BclI fragment spanning positions 11,207 and 14,711, having ocs, a 3'-deleted tml, and the right border of $T_L$. p233 was linearized with SmaI, mixed with and ligated to a commercially available blunt-end BglII linker, trimmed with BglII, religated to itself, and transformed into E. coli GM33 (a dam- host that does not methylate DNA in a manner incompatibles with the action of BclI, Marinus MG and Morris NR (1974) J. Mol. Biol. 85.:309–322). A colony was identified which harbored a plasmid, designated p233G, having a BglII site in the location formerly occupied by the position 11,207 SmaI site.

p102 is a plasmid having T-DNA spanning the HindIII sites at T-DNA positions 602 and 3,390 inserted into the HindIII site of pBR322. T-DNA near position 602 is proximal to the pBR322 EcoRI site while T-DNA near position 3,390 is proximal to the pBR322 SalI and BamHI sites. The 3.5 kbp BclI/DglII fragment of p233G, which carries border repeat B, ocs, and the 5'-end of tml, was mixed with and ligated to p102 DNA that had been dephosphorylated after digestion with BamHI and BglII. The ligation mixture was transformed into E. coli. Plasmid DNAs isolated from ampicillin-resistant transformants were screened by restriction analysis and a colony was identified which harbored a plasmid designated pAR2. pAR2 has the following structure:

. . . amp . . . EcoRI . . . pBR322 position 29 HindIII pTi15955 position 602 . . . T-DNA position 1,617 BglII T-DNA position 11,207 . . . T-DNA position 14,711 (BclI/BamHI) pBR322 position 375 . . . pBR322 position 651 SalI . . . ori . . . amp . . .

In other words, two pTI15955 fragments were inserted between the HindIII and BamHI sites of pBR322, a HindIII/BglII fragment spanning T-DNA positions 602 to 1,617 and a BglII/BclI-fragment spanning T-DNA positions 11,207 to 14,711 (the BglII site having been converted from a SmaI site at position 11,207), the two T-DNA fragments being ligated together at their BglII-derived ends to form a BglII-cleavable suture. These two T-DNA fragments were inserted so that the HindIII-end of the T-DNA was joined to the pBR322 position 29 HindIII site, thereby forming a HindIII-cleavable suture, and the BclI-end of the TDNA was joined to the pBR322 position 375 BamHI site, thereby forming a suture that could not be cut by either BamHI or BclI.

pAR2 was digested with SalI, thereby being linearized at the pBR322 position 651 SalI site. Sticky-ends of the linearized DNA were converted to blunt-ends by incubation with the klenow fragment of DNA polymerase I, this DNA was mixed with and ligated to commercially available HindIII linkers. After partial digestion with HindIII and religation of the mixture to itself, the mixture was transformed into E. coli. Plasmid DNAs isolated from ampicillin-resistant transformants were screened by restriction analysis and a colony was identified which harbored a plasmid designated pAR-Sal (FIG. 8). pAR-Sal was identical to pAR2 except for conversion of the pAR2 SalI site to the specificity of HindIII (one or more HindIII sites may be present at this location). A 4.8 kbp HindIII fragment could be isolated from pAR-Sal which carried the T-DNA of a micro-Ti, having between Borders A and B the ORF1 promoter, a unique BglII site, the 5'-end of a tml gene, and a functional ocs gene.

pDOB513K4.6 DNA, whose construction is detailed below, was digested with BglII and a 3.26 kbp fragment carrying the CaMV 19S promoter/NPT2 structural gene/CaMV and T-DNA polyadenylation sites combination was electrophoretically isolated. This BglII fragment was mixed with and ligated to BglII-linearized, dephosphorylated pAR-Sal DNA. The ligation mixture was transformed into E. coli. Plasmid DNAs isolated from ampicillin resistant transformants were restriction mapped and a colony was isolated which harbored a plasmid, designated. pCT-29, that had the promoter/NPT2 gene/polyadenylation site combination inserted into the BglII site of pAR-Sal. The combination was oriented so that it was transcribed parallel. to the 5'-end of tmt and the ocs gene and antiparallel to the ORF1 promoter. pCT-29 had two BglII sites.

Kanamycin resistance is a useful genetic marker to use when transforming Agrobacterium. As the CaMV promoter/NPT2 structural gene combination is not expressed in bacteria, it was useful to include a kan gene in the micro-Ti cassette. A neomycin phosphotransferase I (NPT1) gene from Tn903 is present on pUC4K (Vieira .J and Messing J (1982) Gene 19:259–268). pUC4K DNA was digested with BamHI and 1.45 kbp fragment carrying an NPT1 gene was electrophoretically isolated. This BamHI fragment was mixed with a ligated to linear, dephosphorylated pCT-29 DNA that had been linearized with BglII under partial digestion conditions. The ligation mixture was transformed into E. coli. Restriction mapping of plasmid DNAs led to identification of an ampicillin-resistant, kanamycin-resistant transformant which harbored a plasmid designated pCT29K-2. pCT29K-2 has an NPT1 gene that is expressible in bacteria inserted into the BglII site found between the ORF1 promoter and the NPTII gene. The BglII/BamHI sutures between the pUC4K fragment and the pCT-29 vector could not be cleaved by either BglII or BamHI; pCT29K-2 had only one BglII site, located between the NPT2 and ocs genes. The NPT1 gene was oriented parallel to the ORF1 promoter and antiparallel to the NPT2 gene, the 5'-end of tml, and the ocs gene. pDOB513K4.6, the source of the CAMV 19S promoter NPT2 structural. gene/polyadenylation site combination, was constructed as follows.

The kanamycin resistance gene (kan) of Tn5 encodes the enzyme. neomycin phosphotransferase II (NPT2). The kan gene has been sequenced (Beck E et al. (1982) Gene 19:327–336) and may be extracted from pKS4, a pBR322 derivative. pKS4 DNA may be isolated from E. coli C600 (pKS4) which is on deposit as NRRL B-15394.

pKS4 DNA was digested with SmaI to open it at the Tn5-derived SmaI site. After this linearized DNA was mixed with and ligated to ClaI linkers, the DNA was transformed into E. coli K802. Plasmid DNAs isolated from transformants resistant to ampicillin and kanamycin were screened by restriction mapping and a colony was identified which harbored a plasmid, designated pKS4.2, having a kan gene that could be extracted on a ClaI fragment.

pKS4.2 was digested with ClaI and a fragment carrying the kan gene was electrophoretically isolated. This fragment was mixed with and ligated to ClaI-linearized pBR322 and transformed into E. coli. Plasmid DNAs isolated from transformants resistant to ampicillin and kanamycin were screened by restriction analysis and a colony was identified which harbored a plasmid designated pKS4.3. The pKS4.3 kan gene was oriented with its 5'-end and 3'-end respectively proximal to the pBR322 EcoRI and BamHI sites. In this orientation the kan gene may be removed on a HindIII fragment.

pKS4.3 DNA was digested with HindIII and mixed with and ligated to HindIII-linearized M13mp8 RF DNA (Vieira J and Messing J (1982) Gene 19:259–268). The ligation mixture was transformed into *E. coli* JM107 (Yanisch-Perron C et al. (1985) Gene 33:103–119) and, after isolation of RF DNA from transformants resistant to ampicillin and kanamycin, a colony was identified which harbored a M13-derivative designated M13HS-Kan. M13HS-Kan had the kan gene inserted into the M13mp8 HindIII site parallel to the M13mp8 lac gene. When in viral form, the NPT2 sequence was equivalent to an NPT2-encoding mRNA. In other words, the M23HS-Kan single-stranded viral DNA could not hybridize to NPT2 mRNA but was complementary to a cDNA made from NPT2 mRNA.

Single-stranded viral DNA was mixed with and hybridized to a primer having the sequence (a) 5'CAATCATGC-GAAAGGATCC3'. (The underlined base indicates the position of the introduced mutation.) After primer extension, this DNA was transformed into *E. coli* JM107. RF DNAs isolated from transformed plaques were screened by hybridization under stringent conditions to $^{32}$P-end-labeled primer and by restriction analysis. A colony was identified which harbored a M13HS-Kan derivative designated M13HS-Kan1 (sm). M13HS-Kan1 had a BamHI site at about −10 relative to the ATG translational start codon. Cutting at this BamHI site removes a Tn5 ATG located approximately at position −15.

The transcript terminators of pTi15955 ORFs 25 and 26 are both located within a DNA segment bounded by HincII sites at positions 21,727 and 22,440, as defined by Barker et al., supra. This 714 bp HincII fragment carries polyadenylation sites of two antiparallel genes, ORFs 25 and 26. When this HincII fragment, or any DNA segment having two antiparallel polyadenylation sites, is placed behind a structural gene, one or the other polyadenylation sites will be functional for promoting transcript termination in a plant cell. This HincII fragment is a subfragment of octopine pTi EcoRI fragment 22.

Some alternative blunt-ended pTi15955-derived segments carrying antiparallel transcript terminators, the restriction enzyme(s) which generate them, and their sizes are as follows:

| ORFs | Enzyme(s) | Size (bp) |
| --- | --- | --- |
| 9/10 | HaeI | 1034 |
| 9/10 | HaeIII | 915 |
| 9/10 | NaeI/SmaI | 807 |
| 21/24 | AluI | 755 |
| 21/24 | ThaI | 960 |
| 25/26 | HaeI | 1163 |
| 25/26 | PvuII/StuI | 1036 |

Nonblunt-ended segments can be obtained and either used directly or have sticky-ends converted to blunt ends by methods well known to the art; e.g., a 1.11 kbp BbvI/ClaI fragment carries terminators of pTi15955 T-DNA ORFs 1 and 3 and a 1.46 kbp NciI fragment carries terminators of ORFs 9 and 10.

A pBR322 clone of the EcoRI fragment spanning T-DNA positions 16,202 to 21,631 was digested with HincII. A 714 bp HincII fragment carrying the ORFs 25 and 26 polyadenylation sites was electrophoretically purified. pKS4 DNA digested with SmaI was mixed with and ligated to the 714 bp HincIII fragment. *E. coli* cells were transformed by the ligation mixture. Plasmid DNAs isolated from transformants resistant to kanamycin and ampicillin were screened by restriction analysis. A colony was identified which harbored a plasmid, designated pKS4.5, that had the 714 bp T-DNA fragment inserted into the SmaI site present in the Tn5 sequences of pKS4 3'-from the NPT2-encoding sequence.

pKS4.5 DNA was digested with HindIII and NcoI. This operation deleted the 5'-end of the NPT2 gene along with some 5'-flanking sequences. The HindIII/NcoI-digested DNA was mixed with and ligated to M13HS-Kan1 RF DNA which had been digested with HindIII and NcoI. After transformation of the ligation mix into *E. coli* and selection for resistance to ampicillin, plasmid DNAs were isolated and screened by restriction analysis. A colony was identified which harbored a plasmid, designated pKS4.6, which was essentially identical to pKS4.5 except for a single-base substitution which created a BamHI site just 5'-to the NPT2 encoding sequence.

pDOB512, carrying cauliflower mosaic virus (CaMV) transcription controlling sequences (obtained from Dr. Ken Richards, Centre National de la Recherche Scientifique, Institute de Biologie Moleculaire et Cellulaire, 15, rue Descartes, F-67084 Strasbourg, France) was constructed as follows: (For a review of CaMV, see Hohn T et al. (1982) Curr. Top. Microbiol. Immunol. 96:193–236.) A HindIII fragment carrying the CaMV 19S RNA promoter region (CaMV nucleotides 5376–5851) was inserted into pBR322 and was trimmed back to within one base pair of the 19S transcript cap site. An adapter molecule having both a SmaI site and a BamHI (the structure being 5'CCCGGGGATCCGG3':5'CCGGATCCCCGGG3') was then ligated to the trimmed DNA. A HincII fragment carrying the CaMV 19S transcript terminator (CaMV nucleotides 7018–7794) to which BamHI linkers had been added was then inserted behind the 19S promoter, the promoter and terminator being separated by the SmaI/BamHI linker. The resulting plasmid is designated pDOB412. pDOB412 DNA was digested with BglII and SalI, filled in by incubation with the Klenow fragment of *E. coli* DNA polymerase I, and religated, thereby deleting DNA, which includes BamHI and HindIII sites, between the CaMV position 7644 BglII site and the pBR322 position 650 SalI site and regenerating a BglII site. The resultant plasmid was designated pDOB512.

The sticky-ends of HindIII-linearized pDOB512 DNA were converted to blunt-ends. The blunt-ended pDOB512 DNA was mixed with and ligated to commercially available BglII linkers. The ligation mix was transformed into *E. coli* K802 and an ampicillin-resistant transformant was isolated which harbored a plasmid, designated pDOB513.

The NPT2 structural gene was removed from pKS4.6 (single mutant: BamHI site present but the C at −3 not changed to an A) by digestion with BamHI. After the 2.23 bp fragment was electrophoretically isolated, it was mixed with and ligated to BamHI-linearized, dephosphorylated pDOB513 DNA. The ligation mixture was transformed into K802. Plasmid DNAs isolated from ampicillin-resistant transformants were screened by restriction mapping and a colony was identified which harbored a plasmid designated pDOB513K4.6. The NPT2 structural gene of this plasmid was oriented with its 5'-end proximal and its 3'-end distal to the CaMV 19S promoter. The T-DNA of pCT29K-2 can be represented as follows:

borderA . . . bacteria-selectable NPT1 . . . unique BglII site . . . plant-selectable NPT2 . . . 5'-end of tml . . . ocs . . . border B.

Except for NPT1 (NPT1 is neomycin phosphotransferase I, NPT2 is neomycin phosphotransferase II), all of these genes are transcribed in the same direction. This T-DNA can be removed from pCT29K-2 on a 9.52 kbp Hind III fragment.

The micro-T-DNA-carrying 9.52 kbp (kilobase pair) HindIII fragment of pCT29K-2 was mixed with and ligated to HindIII-linearized, dephosphorylated pTJS75 DNA (see Klee, H. J. et al. (1985) Biotechnol. 3:637–642). Restriction mapping of *E. coli* transformants resistant both to kanamycin and to tetracycline resulted in identification of a colony harboring a plasmid designated pH575 (FIG. 1).

Example 2

Preparation of phaseolin gene p121 (Murai, N. et al. (1983) Science 222:476–482) has the pTi15955 BamHI fragment spanning positions 9,062 and 13,774. (T-DNA positions are as reckoned by Barker, R. F. et al. (1983) Plant Mol. Biol. 2:335–350) inserted into the BglII site of pRK290 (Ditta, G. et al. (1980) Proc. Natl. Acad. Sci. U.S.A. 77:7347–7351). The T-DNA Position 11,207 SmaI site had been converted to a HindIII site and a 6.8 kbp HindIII fragment having a phaseolin gene on a 3.8 kbp BamHI/BglII segment carried by p3.8 (AGPVPh3.8 of Slightom, J. L. et al. (1983) Proc. Natl. Aced. Sci. U.S.A. 80:1897–1901), a Tn5 kanamycin resistance gene (kan), and some pBR322 sequences; both the phaseolin and kan genes are oriented parallel to the T-DNA tml gene. p121 is described in greater detail by Hall, T. C. et al., European Publication No. 0122791, wherein it is designated p499/6/7. *E. coli* K802(p499/6/7) has been deposited as NRRL-15384.

Example 3

Insertion of methionine codons into phaseolin gene p121 has a single XbaI site which is within the third phaseolin exon at about 805 as reckoned by Slightom, et al., supra. XbaI-linearized, p121 DNA was mixed with and ligated to a phosphorylated synthetic oligonucleotide having the following duplex structure:

5'CTAGACCAGATGAGAATGATGGACCAGATGAG
GATGATGGACGTT3'
3'TGGTCTACTCTTACTACCTGGTCTACTCCTACTA
CCTGCAAGATC5'

This oligonucleotide encodes 15 amino acids and has a composition of Arg$_2$AspaGln$_2$LeuMet$_6$Val, basically representing a duplication of a 15 kD zein sequence encoded by DNA residues 271–291, reckoned as described by Pederson, K. et al.(1986) J. Biol. Chem. 261:6279–6284, inserted into the phaseolin structural gene. This particular 15 kD zein peptide was chosen for its high content of methionine and its alpha-helical structure as predicted by the well known algorithm of Chou and Fasman. This oligonucleotide also contained a FokI restriction site useful for detecting and determining the orientation of the insert, and six methionine codons. When inserted into the phaseolin gene, this oligonucleotide triples the quantity of methionine encoded thereby. (The mature phaseolin polypeptide encoded by the unmodified gene contains three methionine residues, the two methionine residues at the amino terminus being removed by posttranslational processing of the signal peptide.) After ligation the modified phaseolin gene has the structure as shown in Table 1:

TABLE 1

| ...phaseolin | 808 271 →← | zein | 288 271 →← | zein | 291 805 →← | phaseolin... |
|---|---|---|---|---|---|---|

...His Ile Leu Asp Gln Met Arg Met Met Asp Gln Met Arg Met Met Asp Val Leu Glu Ala...
5'...CATATTCTAGACCAGATGAGAATGATGGACCAGATGAGGATGATGGACGTTCTAGAGGCC...3'
3'...GTATA<u>AGATCT</u>GGTCTACTCTTACTACCTGGTCTAC<u>TCCTAC</u>TACCTGCA<u>AGATCT</u>CCGG...5'
       XbaI                               FokI            XbaI

The uppermost portion of the above representation indicates the protein from which the sequence below the line was derived, with the numbers on the ends of the lines indicating the coordinate of the end of the segment as reckoned by Pederson et al. for zein and Slightom et al. for phaseolin. Note that duplication of the XbaI site lead to duplication of a phaseolin leucine residue encoded thereby, and that the Asp-Gln doublet in the middle of the insertion is duplicated at the 5'-end of the insert. The ligation mixture was transformed into *E. coli* MC1061 and selected for resistance to tetracycline. Colonies containing the oligonucleotide were identified by hybridization with $^{32}$P-labeled oligonucleotide. A colony was identified by restriction mapping of DNA isolated therefrom which harbored a plasmid, designated p121(+45) (FIG. 1), having the insertion in the orientation so that it encoded an amino acid sequence as indicated above.

Example 4

Placement of phaseolin gene between Bam HI sites p121(+45) DNA was digested with HindIII and a 6 kbp fragment carrying the phaseolin gene/kan combination was electrophoretically isolated. This 6 kbp fragment was mixed with and ligated to HindIII-linearized pSP64 (FIG. 1) DNA (Melton, D. A. et al. (1984) Nucl. Acids Res. 12:7035–7056). After transformation into *E. coli* MC1061, DNAs isolated from transformants resistant to ampicillin and tetracycline were characterized by restriction mapping. A colony was identified which harbored a plasmid designated pSPhiPneo (FIG. 1) having the modified phaseolin on a 4.1 kbp BamHI fragment in pSP64.

The above operations were also done with p121 substituting for p121(+45) as a starting material. This resulted in identification of a colony which harbored a plasmid designated pSPPneo (FIG. 1) lacking the 45 bp (base pair) insertion in the phaseolin gene but was otherwise identical to pSPhiPneo.

Example 5

Insertion of phaseolin gene into a micro-Ti

BamHI-digested pSPhiPneo DNA was mixed with and ligated to BglII-linearized pH575 DNA. After transformation into *E. coli*, DNAs isolated from tetracycline-resistant transformants were characterized by restriction analysis. A colony was identified which harbored a plasmid, designated pH5hiP (FIG. 1), having the modified phaseolin gene inserted into the pH575 T-DNA.

The above operations were also done with pSPPneo substituting for pSPhiPneo as a starting material. This resulted in identification of a colony which harbored a plasmid designated pH5P (FIG. 1). pH5P lacked the 45 bp insertion in the phaseolin gene but was otherwise identical to pH5hip. pH5P served as a wild-type phaseolin control for the pH5hiP mutant.

Example 6

An alternative manipulation of phaseolin

A somewhat simpler construction is also possible. p3.8 is opened at its sole XbaI site which is located within the phaseolin gene. The 45 bp insert is then ligated into the phaseolin gene. This modified gene can be removed on a 3.8 kbp BamHI/BglII fragment and be inserted into the BglII site of pH575. The resulting high methionine phaseolin gene-carrying micro-Ti plasmid is virtually identical with pH5hiP, differing only in some sequences 5'- from the phaseolin gene. p3.8 can also be used to make a control plasmid virtually identical to pH5P.

Example 7

Plant transformation pH5hiP and pH5P were individually transferred into A. tumefaciens LBA4404 (Ooms, G. et al. (1981) Gene 14:33–50), a vir gene-harboring, micro-Ti-mobilizing strain, by the triparental mating technique (Ruvkun, G. B. and Ausubel, F. M. (1981) Nature 289:85–88), which is well-known in the art. Tobacco leaf tissue was obtained from 4- or 5-week old *Nicotiana tabacum* var. Xanthi$^{Nc}$ plants grown in a greenhouse. Inoculation was by a modification of the method Horsch, R. B. et al. (1985) Science 227:1229–1231. Inocula were prepared by placing two loopfuls of agrobacteria in 10 ml of broth. After suspension by forceful pipetting with a Pasteur pipet, inocula could be used immediately. Leaves were excised and midribs were removed; cutting surfaces were wetted with L-broth to help keep the leaves wet. Leaf pieces were about 2–4 mm wide and about 7–10 mm long. Leaf pieces were dipped in the inoculum for 5–10 min., though in some experiments, leaf pieces were just dipped into the inoculum or were infiltrated with the inoculum in a vacuum flask. Pieces were then blotted dry on sterile filter paper and placed upside down on feeder plates prepared from a Xanthi suspension culture. The feeder plates had a SMPi medium (SMPi: MX$^-$ supplemented with 0.1 mg/l p-chloro-phenoxyacetic acid (pCPA) and 7.5 rag/l 6-(8,8-dimethylallylamino)purine (2iP); MX$^-$: 1.65 g/l $NH_4NO_3$, 1.9 g/l $KNO_3$, 440 mg/l $CaCl_2 \cdot 2H_2O$, 370 mg/l $MgSO_4 \cdot 7H_2O$, 170 mg/l $KH_2PO_4$, 0.83 mg/l KI, 6.2 mg/l $H_3BO_3$, 22.3 mg/l $MnSO_4 \cdot 4H_2O$, 8.6 mg/l $ZnSO_4 \cdot 7H_2O$, 0.25 mg/l $Na_2MoO_4 \cdot 2H_2O$, 0.025 mg/l $CuSO_4 \cdot 5H_2O$, 0.025 mg/l $CoCl_2 \cdot 6H_2O$, 1 g/l inositol, 50 mg/l nicotinic acid, 50 mg/l pyroxidine•HCl, 50 mg/l thiamine•HCl, 30 g/l sucrose, pH 5.8, solidified with 8 g/l agar). Leaf pieces were removed from feeder plates after 4–6 days and placed on SMPi medium supplemented with 500 mg/l carbenicillin, 50 mg/l cloxacillin, and 100–300 mg/l kanamycin (200 mg/l optimum). The resulting shoots were excised and placed on MX medium supplemented with 100–300 mg/l kanamycin (200 mg/l optimum).

Example 8

Expression in plants

Regenerated tobacco plants descended from cells transformed by A. tumefaciens LBA4404 (pH5hiP) or A. tumefaciens LBA4404 (pH5P) were self-fertilized. The resulting seeds can be germinated on MX$^-$ supplemented with 100–300 mg/l kanamycin (200 mg/l optimum) to select plants containing the nonmonocot promoter/monocot seed storage protein structural gene-bearing T-DNA. Presence of the transformed T-DNA was confirmed by Southern blot analysis. Presence of the transformed T-DNA was confirmed by Southern blot analysis. Presence of mRNA encoding modified or unmodified phaseolin can be confirmed by Northern blot analysis. Presence of phaseolin protein in developing tobacco seeds was detected by SDS-polyacrylamide gel electrophoresis followed by transfer to membrane filters and immunological detection (western blots). Modified phaseolin was observed in seeds of plants transformed by pH5hiP. The phaseolin promoter is known to be able to express phaseolin in tobacco seeds at levels above about 0.05% total protein levels, often at a level of about 1% protein.

I claim:

1. A method for producing a modified 7S legume seed storage protein in a plant cell which comprises the steps of (a) modifying a DNA sequence of a structural gene encoding a 7S legume seed storage protein, wherein said structural gene comprises a conserved region corresponding to the conserved region of a phaseolin gene that flanks an XbaI site, by inserting a nucleotide sequence comprising a methionine codon into said conserved region;

(b) transforming a plant cell with the modified 7S legume seed protein structural gene such that the modified structural gene is expressible in a plant cell; and (c) regenerating a plant descended from the transformed plant cell, whereby a plant that expresses the modified 7S legume seed storage protein structural gene is produced.

2. A plant produced by the method of claim 1.

3. A seed of a plant of claim 2 which comprises said DNA sequence encoding the modified 7S legume seed storage protein.

4. Progeny of the plant of claim 2 which comprises said DNA sequence encoding the modified 7S legume seed storage protein.

* * * * *

UNITED STATES PATENT AND TRADEMARK OFFICE
CERTIFICATE OF CORRECTION

Page 1 of 3

PATENT NO. : 5,576,203

DATED : November 19, 1996

INVENTOR(S) : Leslie M. Hoffman

It is certified that error appears in the above-identifie d patent and that said Letters Patent is hereby corrected as shown below:

Column 2: Line 8: "resemblingcanonical" should read --resembling canonical--.

Column 3: Line 5: "β-conglyconin" should read --β-conglycinin--; Line 6: "hemology" should read --homology--; Line 48: ", Such" should read --, such--; Line 49: "modificatioh" should read --modification--; Line 57: "structural. gene," --structural gene--.

Column 4: Line 44: "the. location" should read --the location--; Line 64: "homologous.to the" should read --homologous to the--.

Column 5: Line 10: "and. sites" should read --and sites--; Line 49: "hergin to the part-of" should read --herein to the part of--; Line 61: "plants-expressible" should read --plant-expressible--.

Column 7: Lines 34: "termS." should read --terms.--; Line 55: "sequences. may affect" should read --sequences may affect--.

Column 8: Line 9: "the. small" should read --the small--; Line 10: "maybe useful" --may be useful--; Line 48: "on. a "helper" should read --on a "helper"--; Line 50: "accomplished. either" should read --accomplished either--.

UNITED STATES PATENT AND TRADEMARK OFFICE
CERTIFICATE OF CORRECTION

PATENT NO.    :    5,576,203

DATED    :    November 19, 1976

INVENTOR(S)    :    Leslie M. Hoffman

It is certified that error appears in the above-identifie d patent and that said Letters Patent is hereby corrected as shown below:

Column 9: Line 31: "viral, coat" should read --viral coat--; Line 36: "SyStems" should read --systems--.

Column 10: Lines 21&22: "in, this Specification" should read --in this Specification--; Line 25:"and, culture" should read --and culture--.

Column 11: Line 18: "incompatibles" should read --incompatible--; Line 28: "BclI/Dgl II" should read --BclI/Bgl II--; Line 53: "TDNA" should read --T-DNA--.

Column 12: Lines 19&20: "parallel. to the5'-end of tmt gene," should read --parallel to the 5'-end of tml gene,-- Line 27: "(Vieira.J and Messing J" should read --(Vieira J and Messing J--; Line 46: "structural. gene/" should read --structural gene/--; Line 49: "enzyme. neomycin"; should read --enzyme neomycin--.

UNITED STATES PATENT AND TRADEMARK OFFICE
CERTIFICATE OF CORRECTION

PATENT NO. : 5,576,203

DATED : November 19, 1996

INVENTOR(S) : Leslie M. Hoffman

It is certified that error appears in the above-identified patent and that said Letters Patent is hereby corrected as shown below:

Column 15: Line 60: "$Arg_2Asp_aGln_2LeuMet_6Val$" should read --$Arg_2Asp_3Gln_2LeuMet_6Val$".

Column 17: Line 53: "7.5 rag/1" should read --7.5 mg/1--.

Signed and Sealed this

Fifth Day of August, 1997

Attest:

BRUCE LEHMAN

*Attesting Officer*          *Commissioner of Patents and Trademarks*